United States Patent [19]

Possis

[11] E Re. 31,040

[45] Reissued Sep. 28, 1982

[54] HEART VALVE PROSTHESIS

[75] Inventor: Zinon C. Possis, Edina, Minn.

[73] Assignee: St. Jude Medical, Inc., St. Paul, Minn.

[21] Appl. No.: 121,674

[22] Filed: Feb. 15, 1980

Related U.S. Patent Documents

Reissue of:

[64] Patent No.: 4,078,268
Issued: Mar. 14, 1978
Appl. No.: 720,776
Filed: Sep. 7, 1976

U.S. Applications:

[63] Continuation-in-part of Ser. No. 571,285, Apr. 24, 1975, abandoned.

[51] Int. Cl.[3] ..... A61F 1/22

[52] U.S. Cl. ..... 3/1.5; 137/512.1; 137/527.8

[58] Field of Search ..... 3/1.5; 137/512.1, 527, 137/527.8

[56] References Cited

U.S. PATENT DOCUMENTS

| | | | |
|---|---|---|---|
| 15,192 | 6/1856 | Peale | 137/844 |
| 202,725 | 4/1878 | Heister | 417/556 |
| 233,454 | 10/1880 | Wolff | 210/116 |
| 1,087,981 | 2/1914 | Reynolds | 137/512.1 |
| 1,306,391 | 6/1919 | Romanoff | 137/512.15 |
| 1,708,907 | 4/1929 | Spencer | 137/512.1 |
| 2,292,003 | 8/1942 | Yant et al. | 137/512.15 |
| 2,393,170 | 1/1946 | Kinney et al. | 138/37 |
| 2,505,757 | 5/1950 | Dunbar et al. | 137/512.1 |
| 2,682,057 | 6/1954 | Lord | 3/1.5 |
| 2,800,920 | 7/1957 | Smith | 137/512.15 |
| 2,856,956 | 10/1958 | Smolensky | 137/512.1 |
| 2,877,792 | 3/1959 | Tybus | 137/512.1 |
| 2,956,582 | 10/1960 | Pranter | 137/512.1 |
| 3,007,488 | 11/1961 | Wheeler, Jr. | 137/515.7 |
| 3,009,475 | 11/1961 | Richterkessing et al. | 137/512.1 |
| 3,026,901 | 3/1962 | Wheeler, Jr. | 137/454.2 |
| 3,034,715 | 4/1963 | Scharres | 235/132 E |
| 3,072,141 | 1/1963 | Wheeler, Jr. | 137/512.1 |
| 3,099,016 | 7/1963 | Edwards | 3/1.5 |
| 3,113,586 | 12/1963 | Edmark, Jr. | 137/512.1 |
| 3,118,468 | 1/1964 | Bochan | 137/846 |
| 3,130,419 | 4/1964 | Edwards | 3/1.5 |
| 3,263,239 | 8/1966 | Edwards et al. | 3/1.5 |
| 3,312,237 | 4/1967 | Mon et al. | 137/512.15 |
| 3,374,804 | 4/1968 | Stegerud | 137/512.1 |
| 3,396,409 | 8/1968 | Melrose | 3/1.5 |
| 3,416,562 | 12/1968 | Freeman | 137/512.15 |
| 3,416,563 | 12/1968 | Lee | 137/519 |
| 3,445,863 | 5/1969 | Wada | 3/1.5 |
| 3,448,465 | 6/1969 | Pierce et al. | 3/1.5 |
| 3,452,778 | 7/1969 | Babcock | 137/512.1 |
| 3,491,376 | 1/1970 | Shiley | 3/1.5 |
| 3,526,005 | 9/1970 | Bokros et al. | 3/1 |
| 3,546,711 | 12/1970 | Bokros | 3/1.5 |
| 3,568,214 | 3/1971 | Goldschmied | 3/1.7 |
| 3,579,642 | 5/1971 | Heffernan et al. | 3/1.5 |
| 3,579,645 | 5/1971 | Bokros | 3/1.5 |
| 3,589,392 | 6/1971 | Meyer | 137/846 |
| 3,594,824 | 7/1971 | Nakib | 3/1.5 |
| 3,636,570 | 1/1972 | Nielson | 3/1.7 |
| 3,685,059 | 8/1972 | Bokros et al. | 3/1.7 |
| 3,689,942 | 9/1972 | Rapp | 3/1.5 |
| 3,737,919 | 6/1973 | Child | 3/1.5 |
| 3,739,402 | 6/1973 | Cooley et al. | 3/1.5 |
| 3,766,567 | 10/1973 | Kahn et al. | 3/1.7 |
| 3,824,629 | 7/1974 | Shiley | 3/1.5 |
| 3,825,957 | 7/1974 | Kaster | 3/1.5 |
| 3,835,475 | 9/1974 | Child | 3/1.5 |
| 3,861,416 | 1/1975 | Wichterle | 137/849 |
| 3,903,548 | 9/1975 | Nakib | 3/1.5 |
| 3,926,215 | 12/1975 | Macleod | 3/1.5 X |
| 3,938,197 | 2/1976 | Milo | 3/1.5 |
| 3,974,854 | 8/1976 | Kurpanek | 137/512 |
| 4,008,710 | 2/1977 | Chmiel | 128/1 D |
| 4,159,543 | 7/1979 | Carpentier | 3/1.5 |

FOREIGN PATENT DOCUMENTS

| | | | |
|---|---|---|---|
| 1180087 | 10/1964 | Fed. Rep. of Germany | 3/1.5 |
| 321491 | 11/1929 | United Kingdom . | |
| 532241 | 1/1941 | United Kingdom . | |
| 1160008 | 7/1969 | United Kingdom | 3/1.5 |
| 1490492 | 11/1977 | United Kingdom . | |

OTHER PUBLICATIONS

Pierce, Behrendt, and Morrow, "A Hinged Prosthetic Cardiac Valve Fabricated of Rigid Components", *Journal of Thoracic and Cardiovascular Surgery*, vol. 56, No. 2, Aug. 1968, pp. 229–235.

Brewer, "Evaluation of a Double-Leaflet Prosthetic

Heart Valve of New Design for Clinical Use", by Kalke, Lillehei and Kaster, *Prosthetic Heart Valves,* pp. 285–302 and 306–314.

*Primary Examiner*—Ronald L. Frinks
*Attorney, Agent, or Firm*—Low and Low

[57] ABSTRACT

A heart valve prosthesis having an annular base carrying two pivoting valving members for use in a heart to control the flow of blood. The valving members are pivotally mounted on the annular base for pivotal movement about separate axes spaced from the center of the base. In one form of the prosthesis the base is removably attached to a suturing assembly adapted to be connected to heart tissue.

82 Claims, 18 Drawing Figures

HEART VALVE PROSTHESIS

Matter enclosed in heavy brackets [ ] appears in the original patent but forms no part of this reissue specification; matter printed in italics indicates the additions made by reissue.

CROSS REFERENCE TO RELATED APPLICATION

This application is a continuation-in-part of U.S. application Ser. No. 571,285 filed Apr. 24, 1975 now abandoned.

BACKGROUND OF INVENTION

Heart valve prostheses are used as mechanical valve devices to replace damaged or diseased natural heart valves. Known heart valve prostheses have an annular member or base carrying a suturing member adapted to be attached to the heart tissue. One or more valving members associated with the base controls one-way flow of blood through a passage in the base. Retaining means are associated with the valving member to hold the valving member in operative assembled relation with the base. The valving members commonly used are spherical members or balls, pivoting discs, poppet discs and leaflet members. Each of the heart valve prostheses have advantages as well as deficiencies. The operating characteristics of the heart valve prostheses are due mainly to the shape, operating structure and materials of the valving members and base. The limitations of the currently used heart valve prostheses include low efficiency and high pressure gradient across the valve opening, relatively high structural profile, localized sites of wear and fatigue, chemical breakdown and absorption of water and body fluids by the valve materials, regions of blood stagnation, structures that cause turbulence, regurgitation and eddy currents in the blood flow, structures that can cause formation of clots, hemolysis, damage blood tissue, and malfunction of the moving valving member.

Several valve designs have been proposed to use a pair of operating valving members. Mon et al in U.S. Pat. No. 3,312,273 disclose a bicuspid heart valve having a pair of resilient flapper members that move relative to each other to control the flow of blood through the valve passage. A diametrical pin serves as a fulcrum upon which the flapper member moves. Wada in U.S. Pat. No. 3,445,863 discloses a one-way heart valve having a base carrying a pair of valve plates. Each valve plate has a notch for receiving a portion of the base to pivotally mount the valve plate on the base. The valve plate is larger than the opening through the valve base. The valving members move from a generally horizontal position to about 602 relative to the horizontal.

Heffernan et al disclose a heart valve assembly having two flexible flaps that are attached to inside wall portions of the valve body. The flaps flex relative to the body to open and closed positions to control the flow of blood through the valve passage.

A similar split leaflet cardiac valve is shown by Meyer in U.S. Pat. No. 3,589,392. The leaflets have curved shapes and have a flexible hinge portion held on the base. The leaflets flex relative to the hinge position to open and closed positions.

A central flow prosthetic cardiac valve, disclosed by Milo in U.S. Pat. No. 3,938,197, has a plurality of valve flaps pivoted to an annular base. The face is made of five interconnected members.

Servelle shows in British Pat. No. 1,160,008 a heart valve prosthesis having two flaps that are pivotally mounted on a base. An arch extended over the base has an inwardly directed portion which functions as a stop when the flaps are in the open position. A similar heart valve is disclosed by Kalke in the book Prosthetic Heart Valves by Lyman A. Brewer, pages 285–302.

SUMMARY OF INVENTION

The invention relates to a mechanical heart valve prosthesis for controlling the flow of blood in a living heart. The prosthesis has a base provided with a passage for carrying blood. In one form of the prosthesis, a suturing assembly is releasably mounted on the base to secure the prosthesis to the heart tissue. Valving means operably located in the passage controls the one-way flow of blood through the passage. The valving means and base have an overall low structural profile which allows use of the prosthesis in hearts which cannot accommodate conventional ball or disc type heart valve prostheses. The valving means includes a pair of valving members simultaneously movable between closed positions to restrict the flow of blood through the passage in one direction and open positions to allow blood to flow through the passage in the opposite direction. Each valving member has a convex curved leading edge and a transverse trailing edge. First pivot means pivotally mounts the first member on the base for movement about a first axis offset in one direction from the center of the passage. Second pivot means pivotally mounts the second member on the base for movement about a second axis offset in the direction opposite the one direction from the center of the passage. The first axis is parallel to the second axis.

In one form of the invention, the first and second pivot means each have a first and second pair of pivot members secured to the base and projected into the passage. Each pair of pivot members having one pivot member is located adjacent one side of a valving member and a second pivot member located adjacent the other side of the same valving member. Means, as short projections, on the valving member cooperate with at least one pivot member of each pair of pivot members to control the movements of the valving members and retain the valving members in operative relationship with the base.

Each valving member has flat sides that taper toward each other in a downstream direction toward the transverse edge of the member. The shape of the valving members minimizes turbulence and eddy currents in the blood flow pattern. When the valving members are in their open position, blood flows adjacent the opposite sides of each valving member and around the pivot means for the valving members thereby continuously washing all surfaces of the valving members as well as the pivot means. The continuous washing of the surfaces of the valving members and the washing of the pivot means prevents blood clot formation on the surfaces and pivot means. The open valving members are in open positions so that they do not obstruct or interfere with the center flow of blood through the passage.

An object of the invention is to provide a heart valve prosthesis that has (1) a low structural profile which allows the prosthesis to be used in hearts which cannot accommodate conventional ball or disc type heart valve prostheses; (2) a blood flow pattern that has centralized flow and laminar flow through the valve passage and downstream of the passage; (3) a low pressure gradient across the valve; (4) a pair of pivoting valving members that (a) are continuously washed with flowing blood, (b) have shapes that produce a minimum of interference to the flow of blood through the valve passage, a minimum of damage to blood tissues, and a minimum of turbulence and eddy currents in the blood flow pattern, and (c) have fast opening and closing movements and low inertia; (5) a long and reliable life with consistent repetitive operation and is quiet in operation; (6) a minimum of reverse flow to close the valving means and a controlled amount of leakage or back flow when the valving means are closed; (7) no regions where blood can accumulate and stagnate; (8) maximum cardiac output; and (9) a base and suturing member that can be disassembled after the suturing member has been attached to the heart tissue.

IN THE DRAWINGS

DESCRIPTION OF PREFERRED EMBODIMENT

Figure 1:
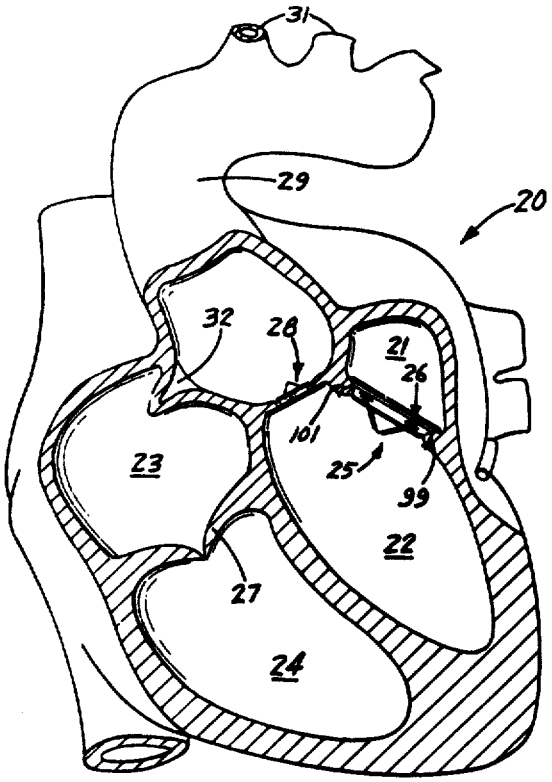
FIG. 1 is a schematic illustration, partly sectioned, of a human heart having a heart valve prosthesis and suturing assembly of the invention in the mitral position.
Figure 2:
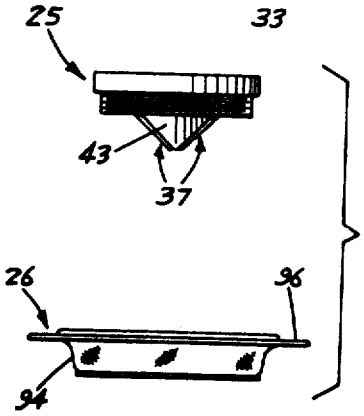
FIG. 2 is an exploded side elevational view of a heart valve prosthesis and suturing assembly of FIG. 1.

Referring to FIG. 1, there is shown a diagram of a human heart 20 having a heart valve prosthesis 25 in the left mitral position. A suturing member 26 releasably attached to the heart valve prosthesis 25 is secured to the heart tissue with suitable sutures. Heart 20 has a left atrium 21 and a left ventricle 22. Heart valve prosthesis 25 is located between the atrium 21 and ventricle 22 in lieu of the natural heart valve. The right atrium 23 is separated from the right ventricle 24 with a natural mitral valve [26] *27*. An aortic heart valve prosthesis 28 is located between the left ventricle 22 and the aorta 29. Aortic valve prosthesis 28 is located inwardly of coronary arteries 32. Prosthesis 28 has the same construction as prosthesis 25. Aorta 29 leads to a plurality of arteries 31.

Figure 3:
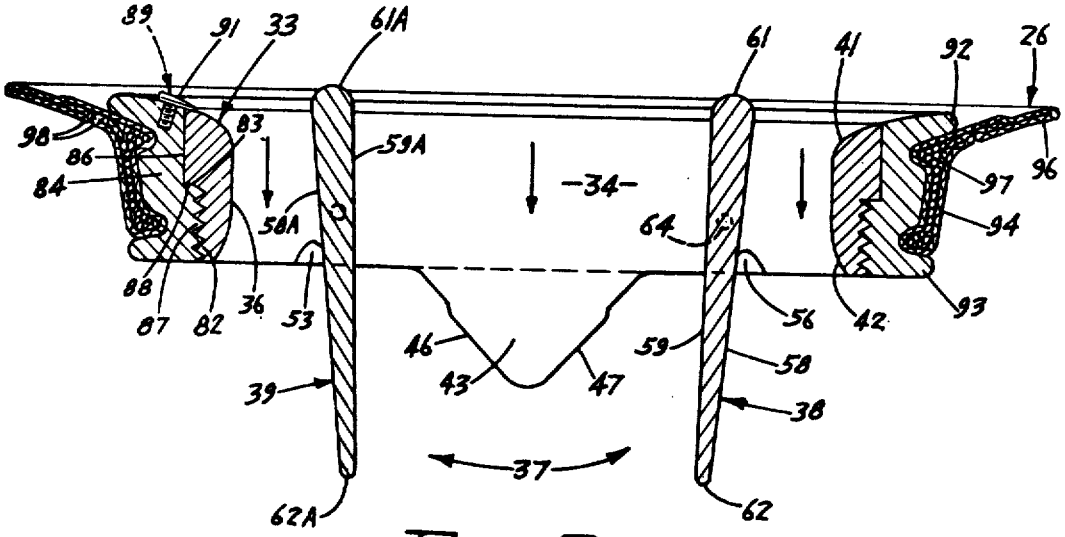
FIG. 3 is an enlarged sectional view of the heart valve prosthesis and suturing assembly in the open position.

Referring to FIG. 3, heart valve prosthesis 25 has an annular base or housing 33 having a passage 34 for carrying the blood from left atrium 21 to left ventricle 22. The housing 33 has a cylindrical inside wall 36 surrounding the passage 34. The flow of blood through passage 34 is controlled with a movable valving means indicated generally at 37. Valving means 37 has a first valving member 38 and a second valving member 39 which move relative to each other from a closed position, as shown in FIG. 5, to an open position, as shown in FIG. 3.

Figure 5:
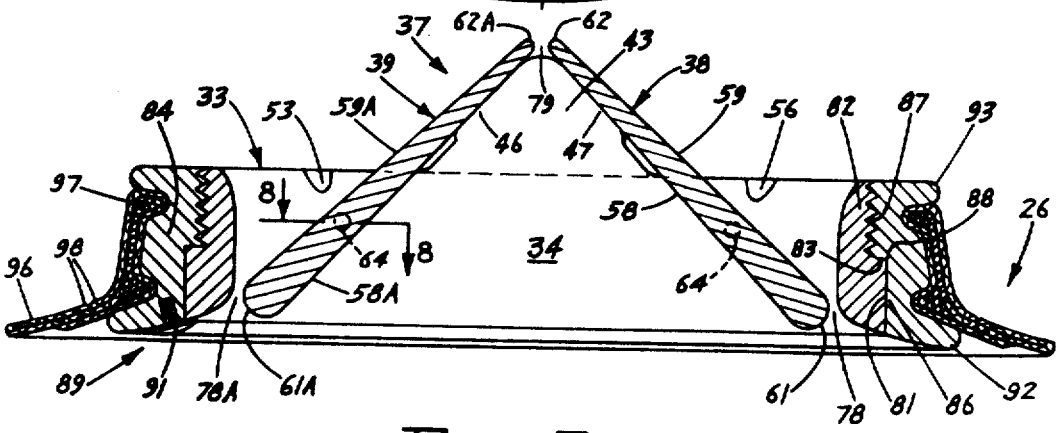
FIG. 5 is a sectional view taken along the line 5—5 of FIG. 4 showing the valve in the closed position.

As shown in FIGS. 3 and 5, base 33 has a convex curve or arcuate inlet end section 41 which joins to the inside cylindrical wall 36. The outlet end sections 42 of the base 33 have a convex curve or arcuate shape whereby the entire passage 34 through the base 33 does not have any abrupt edges or projections which can cause turbulence and eddy currents in the blood flow. Wall 36 and sections 41 and 42 can have other arcuate or curved shapes. A pair of side members 43 and 44 are secured to opposite portions of the base 33. Side members 43 and 44 each have a generally triangular shape and project away from the base 33 in the direction of the flow of blood through the passage 34. Side members 43 and 44 have arcuate shapes in section and are aligned with base 33 so they create only a minimum of interference with the blood flowing through the passage 34. Side member 43 has inclined and converging lip portions 46 and 47 providing short shoulders or seats for portions of the valve members 38 and 39 to hold the valve members in their inclined closed positions, as shown in FIG. 5. The side member 43 has an inside surface 48 that is coextensive with the inside annular wall 36.

Side member 44 has a pair of lip portions or projections 49 and 51 that engage separate portions of the valving members 38 and 39 when the valving members are in their closed positions. Side members 43 and 44 are located on diametrically opposite sides of base 33 and between the pivotal axes of the valving members 38 and 39. The side members 38 and 39 function as barriers to prevent substantial reverse flow of blood through the passage 34 when the valve members 38 and 39 are in their closed positions.

The base has a first pair of stops or projections 53 and 54 which project into the passage adjacent the outside of valving member 39. As shown in FIG. 3, when valving member 39 is in the open position, portions of the valving member 39 engage stops 53 and 54, thereby limiting the open position of the valving member 39. Preferably, valving members 38 and 39 are at 3° with respect to the longitudinal axis of the passage 34 when they are in the open positions. When valving members 38 and 39 are in their closed positions, they are at about 45° with respect to the longitudinal axis of the passage 34. A second pair of stops or projections 56 and 57 are secured to the base 33 and project into passage 34 adjacent the outside surface of valving member 59. As shown in FIG. 3, when valving member 38 is in the open position, outer portions of the valving member engage the stops 56 and 57 to thereby limit the open position of the valving member 38. When the valving members 38 and 39 are in their closed positions, they are at about 45° with respect to the longitudinal axis of the passage 34. In other words, each valving member rotates about 42° between its open and closed positions.

Figure 7:
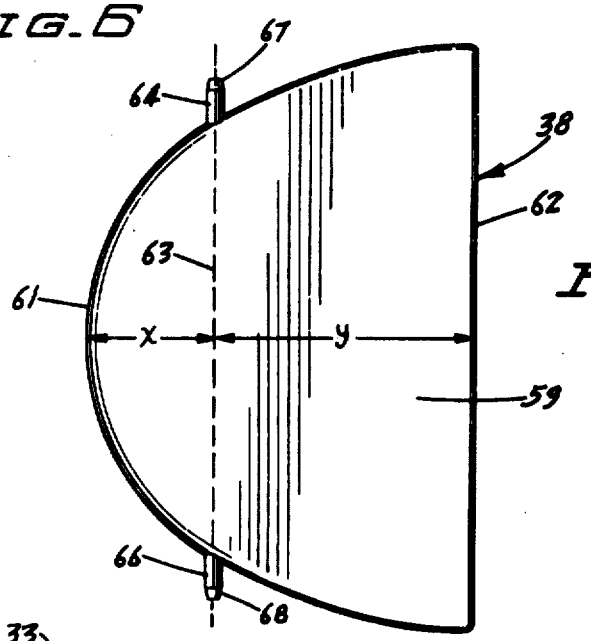
FIG. 7 is a plan view of the side of a valving member.

Referring to FIGS. 3, 5 and 7, the valving member 38 has a semi-elliptical shape with a flat inside surface 58 and a flat outside surface 59. Surfaces 58 and 59 taper toward each other in a downstream direction from a curved front leading edge 61 to a rear transverse trailing edge 62. The front portion of valve member 38 has a thickness that is twice the thickness of the rear or trailing portion adjacent edge 62. The side walls 58 and 59 have a uniform taper from front edge 61 to the rear edge 62. As shown in FIG. 7, the valving member 38 has a transverse pivotal axis shown by broken line 63. Axis 63 coincides with the axis of outwardly directed axles 64 and 66 secured to the outer edge of valving member 38. Each axle has cone-shaped ends 67 and 68, respectively. The axis 63 is located a distance "x" from the midportion of the front wall 61 and a distance "y" from the midportion of the rear edge 62. The distance "y" is twice the distance "x". In other words, axis 63 is one-third of the combined distances "x" and "y" from the midportion of the front edge 61. The mass of valving member 38 is proportioned to balance on axis 63.

Figure 8:
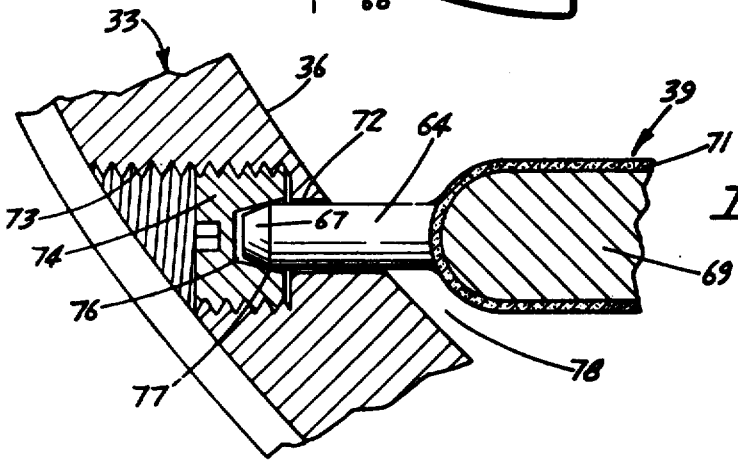
FIG. 8 is an enlarged sectional view taken along the line 8—8 of FIG. 5.

As shown in FIG. 8, valving member 38 has a substrate 69 entirely covered with a coating or skin 71. The substrate 69 can be polycrystalline graphite, plastic, metal or other rigid material. The skin 71 is preferably a silicone alloyed pyrolite carbon. An example of this structure is shown by Bokros in U.S. Pat. Nos. 3,546,711 and 3,579,645. The axles 64 and 66 can also be coated with a pyrolytic carbon material.

Valving member 39 is identical in structure to the valving member 38. The same parts have the same reference numbers with the suffix A.

Axles 64 and 66 of valving member 38 and axles 64A and 66A of valving member 39 are pivotally mounted on the base. The pivot structure for each axle is shown in FIG. 8. Axle 64 extends through a hole 72 open to the inside wall 36 of the base. Hole 72 is coaxial with a threaded bore 73. A bearing plug 74 is threaded into bore 73. The plug 74 has a forward open tapered hole 76 for accommodating the end 67 of the axle 64. The taper of hole 76 is less than the taper of the end 67 whereby there is a circumferential line contact 77 between the axle 64 and bearing plug 74. Plug 74 is made of wear resistant material and may have a skin of pyrolytic carbon.

Figure 4:
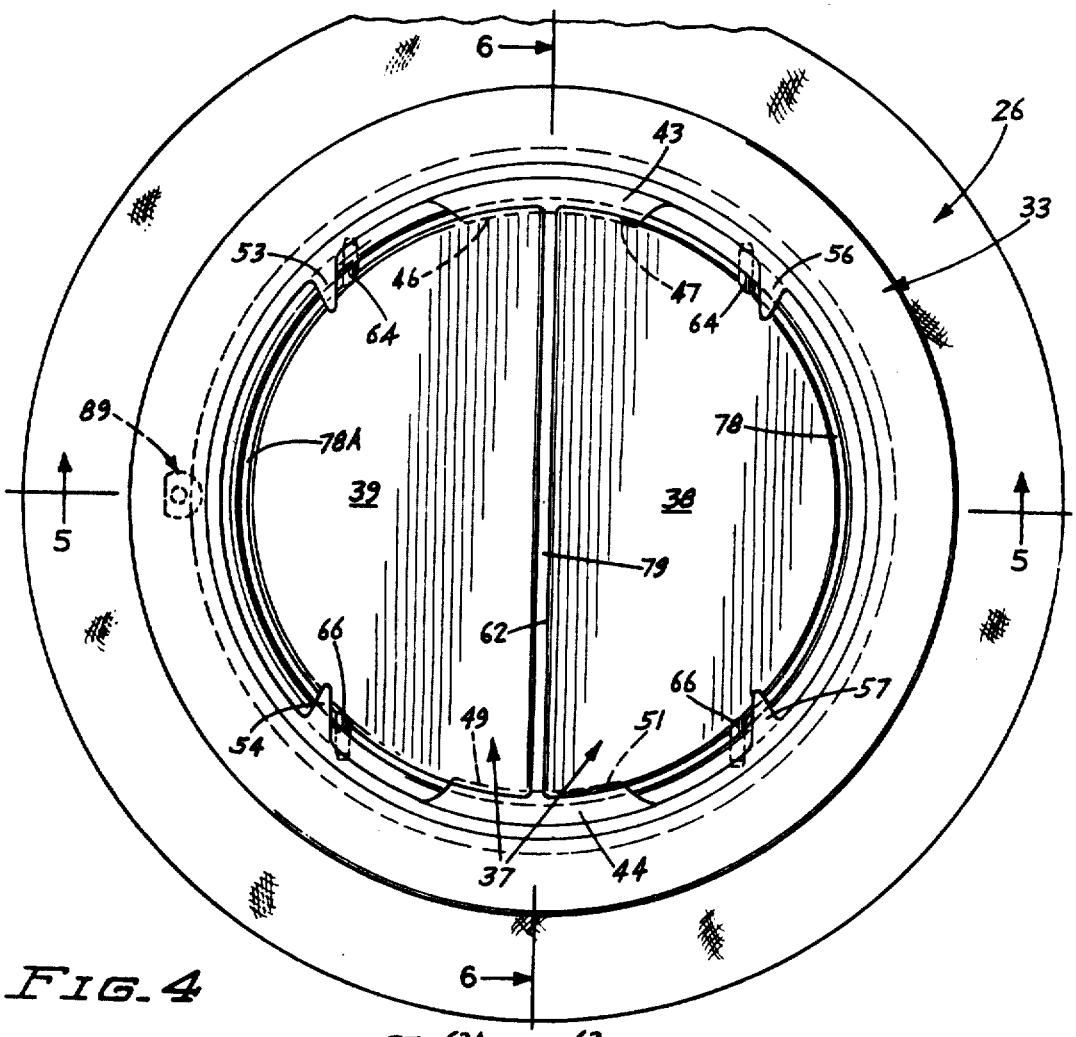
FIG. 4 is a plan view of the bottom of the heart valve prosthesis and suturing assembly shown in FIG. 1.

The valving member 38 is located in the passage 34 with the outer peripheral edges of the valving member being spaced by a space 78 from inside wall 36. Valving member 39 has the same space indicated as 78A between the outer peripheral edge of the valving member and the inside wall 36 of the base. The adjacent transverse trailing edges 62 and 62A are spaced a short distance from each other when the valving members 38 and 39 are in their closed positions. This space is indicated at 78 in FIGS. 4 and 5. Spaces 78, 78A and 79 permit a limited amount of reverse flow or back flow of blood through passage 34 when valving members 38 and 39 are in their closed positions. This provides for a continuous movement of the blood and continuous washing of the surfaces of the valving members, axles 64 and 66, and the inside walls of the valve base, thereby avoiding any areas where blood can stagnate.

Figure 6:
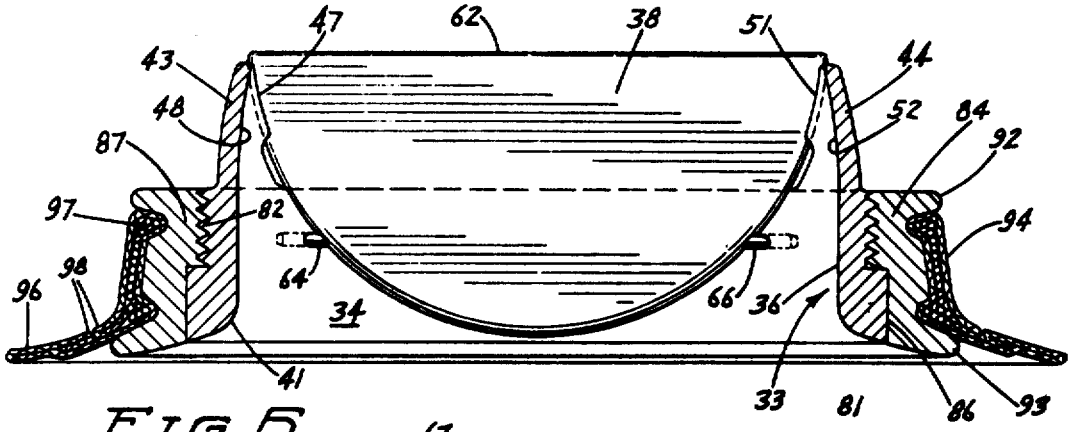
FIG. 6 is a sectional view taken along the line 6—6 of FIG. 4.

Referring to FIGS. 3, 5 and 6, suturing member 26 is releasably mounted on the base 33. This allows base 33 to be removed from suturing member 26 so that suturing member 26 can be attached to the heart tissue and the base subsequently mounted on the suturing member. Also, the heart valve 25 can be removed from the suturing member 26 after the suturing member has been attached to the heart tissue.

Base 33 has an annular outer wall having a first cylindrical portion 81 and a second threaded portion 82. An outwardly directed annular shoulder 83 is located between portion 81 and threaded portion 82. Suturing member 26 has a rigid annular member or sleeve 84 surrounding the base 33. Sleeve 84 is a rigid member of metal, plastic or like material. The inside wall of sleeve 84 has a cylindrical portion 86 and a threaded portion 87. An inwardly directed annular shoulder 88 is located between portion 86 and threaded portion 87. The cylindrical portion 86 is of a size to have a relatively tight fit on cylindrical portion 81. Threaded portion 87 coacts with threaded portion 82 to releasably hold sleeve 84 on base 33. When the sleeve 84 is mounted on the base, the annular shoulders 83 and 88 engage each other and the top and bottom portions of the sleeve are coextensive with the top and bottom portions of the base 33 so that there are no shoulders, projections or abutments which will interfere with the flow of blood through passage 34. Threaded portions 82 and 87 have a plurality of screw thread starts. Preferably the threads are four start threads whereby the base 33 can be mounted on the sleeve in four positions. The number, size and type of threads can vary to achieve the releasable connection between the base 33 and sleeve 84. The plurality of thread starts permits the surgeon to orient the position of the valving members 38 and 39 in the heart. In other words, the circumferential orientation of the valving members 38 and 39 can be selected by the surgeon to provide for the desired direction of flow of blood into the heart chamber and maximum distance between the valving members and any heart tissue. Other types of connecting structures, tongue and grooves, serrations and the like, can be used to mount base 33 on sleeve 84.

The base 33 is held in its assembled position on sleeve 84 with a releasable lock means indicated generally at 89. The releasable lock means includes a screw having a large head 91 that extends over the inlet portion of base 33. Other types of releasable locks can be used to hold the base 33 in a fixed position on sleeve 84. The releasable lock structure shown in Applicant's co-pending U.S. application Ser. No. 572,001 filed Apr. 28, 1975, now U.S. Pat. No. 3,997,923 can be used in lieu of the releasable lock means 89. The releasable lock of this application is incorporated into this specification by reference.

Sleeve 84 has outwardly directed upper and lower flanges 92 and 93 defining a groove for accommodating a collar 94. Collar 94 has an outwardly directed flexible annular flange 96. The collar 94 is a fabric, as "Teflon" or "Dacron". The fabric is biologically inert and does not deteriorate with time. The fabric is preferably interlaced or knitted with spaces into which living neointima tissue grows to form a permanent union between the fabric and the heart tissue independent of the sutures applied by the surgeon. A plurality of cords, surgical strings or threads 97 are wrapped around the collar 94 to hold the collar in the groove structure between flanges 92 and 93. The cords 97 hold the upper and lower portions of collar 94 in engagement with flanges 92 and 93. The collar 94 has turned in ends 98 that are stitched together to cover cords 97. The stitches for the ends 98 are on the inside of the collar, whereby the knots of the stitches are not exposed to the blood, thereby minimizing any clot formations around the suture knots. The materials of the suturing member 26 are sterilizable, biologically inert, non-irritating, non-pyrogenic and non-toxic to body fluids, body tissues and blood tissues.

In use, the heart valve prosthesis 25 is assembled on suturing member 26. Suturing member 26 is secured to the heart tissue with a plurality of sutures 99, as shown in FIG. 1. Valve prosthesis 25 functions on an increase in the blood pressure in the left atrium 21 to open the valving members 38 and 39. As shown in FIG. 3, valving members 38 and 39 open to positions generally parallel or in line with the flow of blood through the passage 34. The blood has unobstructed centralized flow through passage 34. In addition, the blood flows adjacent the outer sides of valving members 38 and 39. The blood washes the inside and outside surfaces of valving members 38 and 39. When the valving members are in their full open positions, they engage the stops 53, 54 and 56, 57 respectively. The valving members 38 and 39 are located about 3° from the longitudinal axis through passage 34.

On reduction of blood pressure in the left atrium 21, the pressure across the heart valve prosthesis is decreased and the flow of blood is reversed. The reversed flow of blood will quickly close the valving members 38 and 39 to the positions shown in FIG. 5. When the valving members 38 and 39 are closed, a small amount of blood will continuously flow around the outer peripheral edges of the valving members 38 and 39 through spaces 78, 78A and 79. This provides for a continuous flow of blood adjacent the inside wall 36 of base 33 and between the adjacent ends 62 and 62A of valving members 38 and 39. This reverse flow minimizes clot formation and provides for continuous washing of the surfaces of the inside wall 36 and the outer peripheral edges of the valving members 38 and 39.

The procedure for mitral valve replacement includes exposure of the heart through a midline sternotomy or a right anerolateral thoracotomy with subteriosteal excision of the fifth rib. The cannulas are placed within the superior and inferior vena cavae via incisions in the right atrium and are maintained there with purse string sutures. The ascending aorta or the femoral artery is used for arterial return flow via another catheter. Ventricular fibrillation is induced electrically before the left atrium is opened to prevent air embolization. A longitudinal left atriotomy allows visualization of the chamber and the mitral valve area. The diseased valve is carefully excised and calcium is removed from the valve annulus and from the outflow track. As shown in FIG. 1, a small annular valvar rim or remnant 101 is retained for accommodating sutures 99 which attach the flange 96 to the heart tissue. The suturing assembly 26 is secured to the remnant 101 with sutures 99. After the suturing member 26 is attached to the heart tissue, valve 25 is attached to the suturing member 26. This is accomplished by inserting base 33 into the sleeve 84 and rotating the base to interconnect the threaded portions 82 and 87. When the base 33 is completely assembled on sleeve 84, the lock means 89 is attached to the sleeve 84 to hold the base in its assembled relation with the sleeve 84. The left atriotomy is then closed and the heart is rewarmed. The heart is defibrillated with AC or DC current, unless this occurs spontaneously.

In the event it is necessary to replace a heart valve prosthesis, the procedure for entering the heart is the same as described above. The heart valve prosthesis is unlocked from sleeve 84 by removing or rotating the lock means 89. The valve base 33 is rotated in the release direction with a tool, thereby separating the base 33 from sleeve 84. The tool can have a handle attached to a pair of plate-like members adapted to engage stops 53, 54 and 56, 57 and the inside wall of the base between the pairs of stops. Rotation of the tool will rotate the base 33. A new valve is then inserted into the sleeve and attached thereto. This is achieved by rotating the base 33 with the tool until the base is aligned or in full assembled relation with the sleeve 84. The lock means 89 is then reattached to sleeve 84 to hold the base in its position relative to the sleeve 84. The valve is replaced without removing the suturing member 26 from the heart tissue.

Referring to FIGS. 9–17, there is shown a modification of the heart valve prosthesis of the invention indicated generally at 125. Prosthesis 125 has an annular base or housing indicated generally at 126 having a circumferential cylindrical inside wall 127. Wall 127 defines a passage 130 through the base for accommodating the flow of blood.

Figure 9:
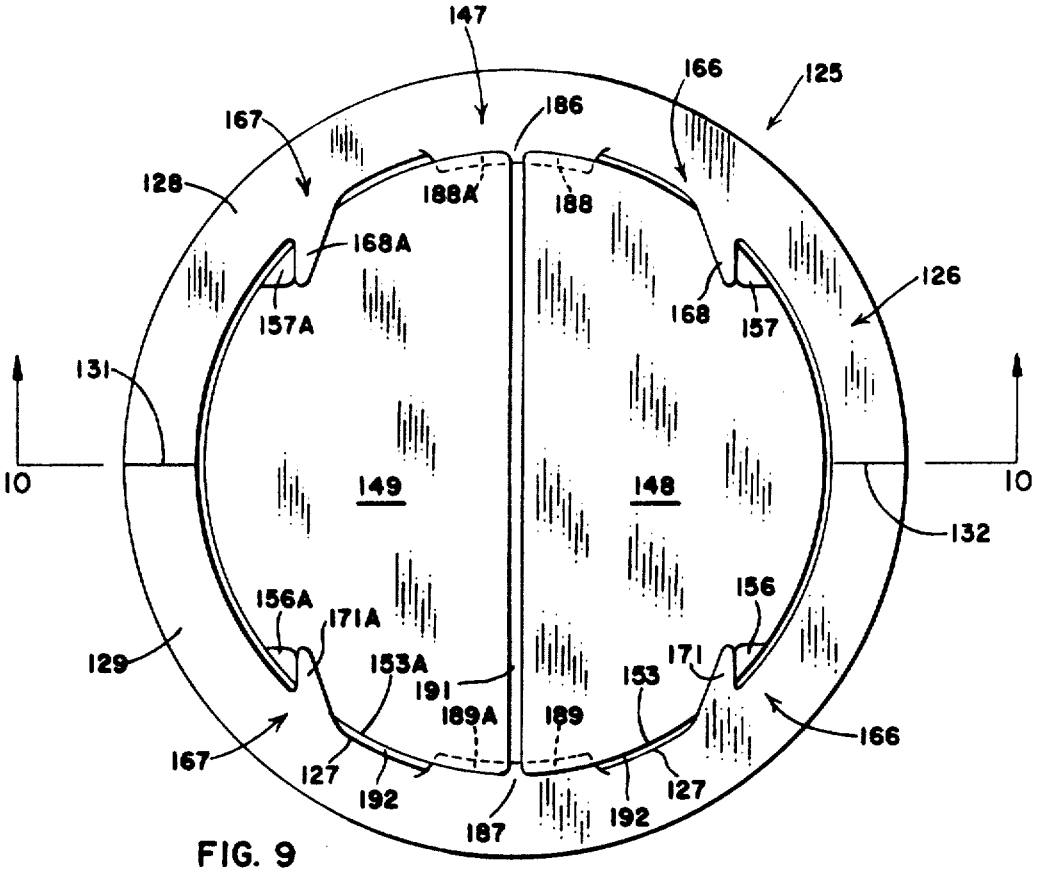
FIG. 9 is a top plan view of a modification of the heart valve prosthesis of the invention.

Base 126 has two semi-circular segments or parts 128, 129 having abutting ends 131, 132. When the semi-circular segments 128 and 129 are located in end-to-end relation, as shown in FIG. 9, they form a circle or annulus. The top portions of the segments 128, 129 have an outwardly directed annular upper or distal flange 133. The segments 128, 129 are held in their circular arrangement with a continuous ring or sleeve 134. The sleeve 134 surrounds the segments 128 and 129 and has a continuous lower or proximal annular outwardly directed flange 136. The flanges 133 and 136 and the outer surface of the sleeve 134 define an outwardly open annular groove 137 for accommodating a suturing member (not shown). The suturing member can be the suturing member 26 as shown in FIG. 3. Other types of suturing members can be mounted on the base to accommodate structures for receiving the sutures used to attach the heart valve prosthesis to the heart tissue.

Figure 10:
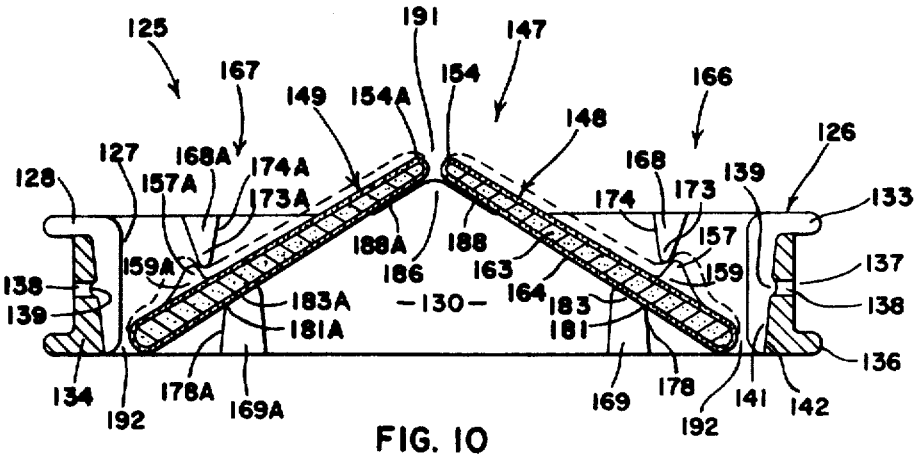
FIG. 10 is a sectional view taken along the line 10—10 of FIG. 9.
Figure 16:
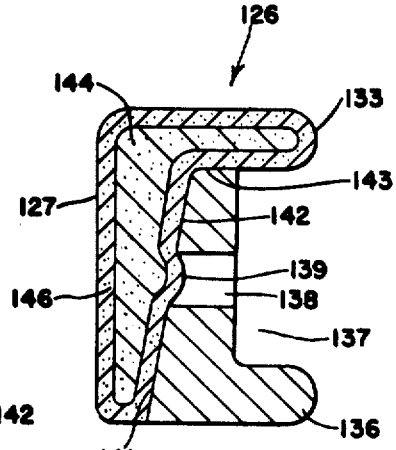
FIG. 16 is an enlarged sectional view taken along the line 16—16 of FIG. 11.

Referring to FIGS. 10, 12, 16 and 17, sleeve 134 has a plurality of radial holes 138. The holes 138 are circumferentially spaced from each other and are located generally in the middle section of sleeve 134. The semi-circular segments 128, 129 each have a plurality of outwardly directed projections or nipples 139 that protrude into the holes 138. The segments 128, 129 have an outside upwardly and outwardly tapered annular surface 141 as shown in FIGS. 10 and 16, that extends to the inner side of the flange 133. Sleeve 134 has an inside tapered surface 142 located in surface engagement with the surface 141 of the segments 128, 129. Sleeve 134 also has a circular upper end 143 located in surface engagement with the lower side of the flange 133. The tapered surfaces 141 and 142 permit the semi-circular segments 128, 129 to be inserted in end-to-end relationship with the ends 131 and 132 in firm engagement in the continuous sleeve 134. The nipples 139 protruding into the holes 138 hold the segments 128 and 129 in firm pressure engagement with the sleeve 134.

Figure 17:
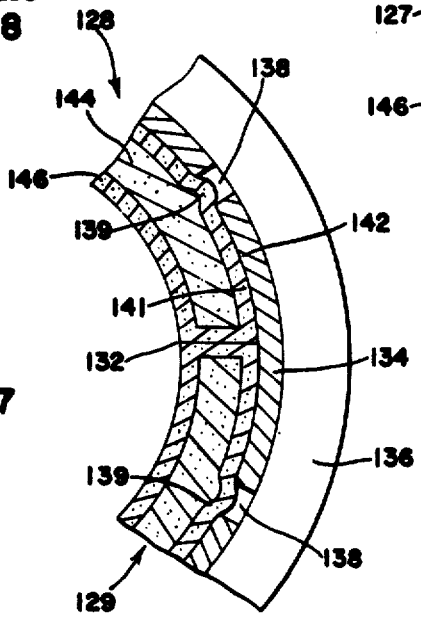
FIG. 17 is an enlarged sectional view taken along the line 17—17 of FIG. 12.

Referring to FIGS. 16 and 17, the arcuate segments 128 and 129 each have a substrate 144 entirely covered with a coating or skin 146. The substrate 144 can be a polycrystalline graphite, plastic, metal or other rigid material. The skin 146 is preferably a silicone alloy pyrolite carbon. An example of this skin material is disclosed by Bokros in U.S. Pat. No. 3,546,711 and U.S. Pat. No. 3,579,645.

Figure 11:
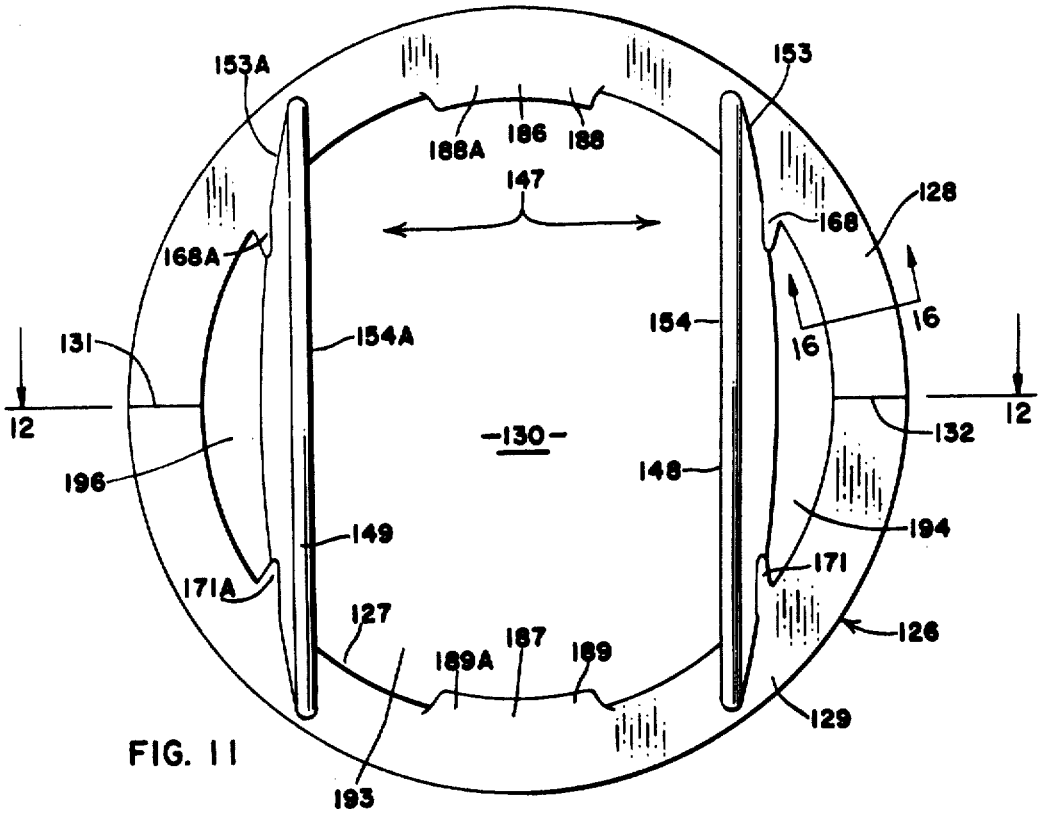
FIG. 11 is a top plan view of the heart valve prosthesis of FIG. 9 with the valving members in their open position.
Figure 12:
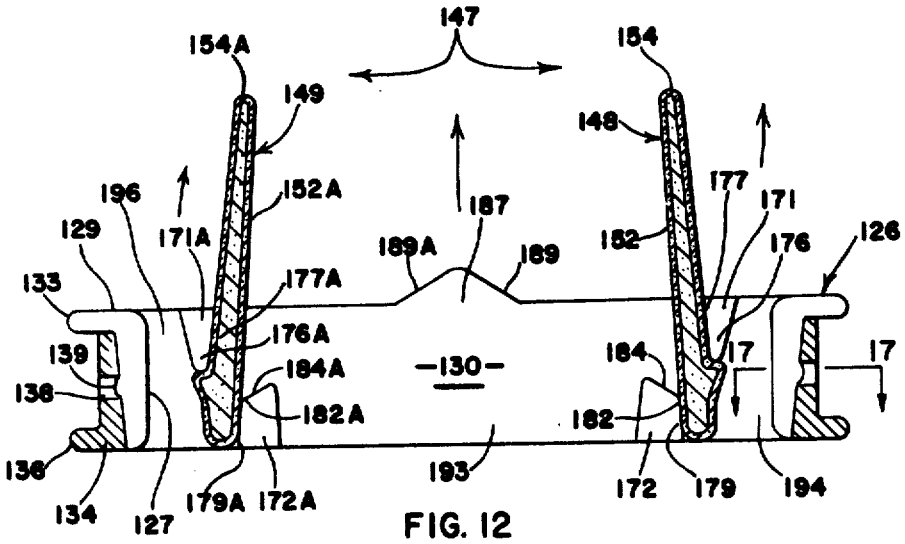
FIG. 12 is a sectional view taken along the line 12—12.

Returning to FIGS. 9–12, the flow of blood through the passage 130 is controlled by a movable valving means indicated generally at 147. Valving means 147 comprises a first valving member 148 and a second valving member 149. Valving members 148 and 149 are operatively positioned in a face-to-face relationship in the passage 130 and are located in a closed position as shown in FIG. 10 to restrict the flow of blood in a downward or reverse direction through the passage 130. Valving members 148, 149 are moved from closed position, shown in FIGS. 9 and 10, to an open position, shown in FIGS. 11 and 12, to permit the substantially unrestricted flow of blood upwardly through the passage 130 of the base 126. Preferably, when the valving members 148 and 149 are in their full open positions as shown in FIGS. 11 and 12, they are located at approximately 3° with respect to the longitudinal axis of the passage 130. When the valving members 148 and 149 are in their closed positions, as shown in FIGS. 9 and 10, they are at about 30° with respect to the transverse horizontal axis of the base 126. The angular inclination of the valving members 148 and 149 can vary. For example, the valving members can be located at 45°, 60° or other angles with respect to the horizontal plane of the base 126.

Figure 13:
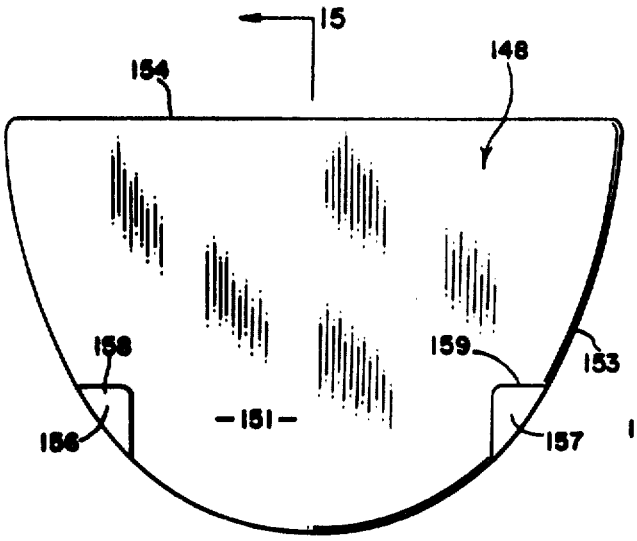
FIG. 13 is a plan view of the side of a valving member of the heart valve prosthesis of FIG. 9.
Figure 15:
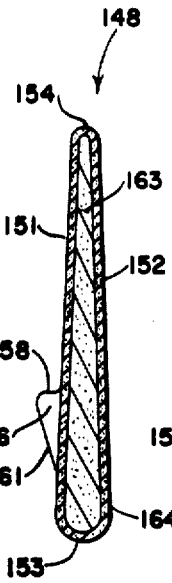
FIG. 15 is a sectional view taken along the line 15—15 of FIG. 13.
Figure 14:
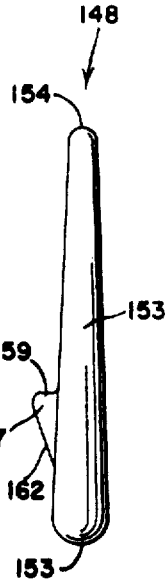
FIG. 14 is a side elevational view of the right side of FIG. 13.

Referring to FIGS. 13–15, there is shown the valving member 148 prior to its assembly with the base 126. Valving member 148 has a general semi-elliptical shape with a flat inside surface 152 and a flat outside surface 151. Surfaces 151 and 152 taper toward each other in a downstream direction from an elliptical curved front leading edge 153. The edge 153 is a continuous uninterrupted outer peripheral edge that terminates at opposite ends of a continuously elongated linear transverse edge 154. The front or leading portion of the valve member 148 has a thickness that is about twice the thickness of the rear or trailing portion located adjacent the transverse edge 154. The side wall surfaces 151 and 152 have a uniform taper from the front edge to the rear transverse edge 154. The edges 153 and 154, as shown in FIG. 14, have a semi-circular or rounded configuration.

A pair of ears 156 and 157 are located on opposite portions of the outside surface 151. The ears 156 and 157 each have a generally triangular shape and transversely aligned faces 158 and 159 respectively. The faces 158 and 159 lie along a line that is located approximately one-third of the combined distance from the transverse edge 154 to the midportion of the edge 153. Each ear has an inclined or tapered back or ramp 161, 162 providing a smooth surface which minimizes interference of the flow of blood through passage 130.

As shown in FIG. 15, valving member 148 has a substrate or core 163 entirely covered with a coating or skin 164. The substrate 163 and coating 164 can be of the same material as the substrate 144 and coating 146 of the base 126.

Valving member 149 is identical in structure and shape to valving member 148. The parts of valving member 149 that correspond to the same parts of valving member 148 have the same reference numbers with the suffix A.

Returning to FIGS. 9–12, valving members 148 and 149 are held in moving assembled relation with the base 126 by pivot and retaining means indicated generally at 166 and 167. Pivot and retaining means 166 cooperates with the valving member 148 to control the opening and closing movements of the valving member 148 and retain the valving member 148 in its moving relation with the semi-circular segments 128 and 129. The pivot and retaining means 167 performs an identical function with respect to the valving member 149.

A pivot and retaining means 166 comprises two pairs of projections or pivot members. The first pair of pivot members comprises an upper member 168 and a lower member 169. As shown in FIG. 10, members 168 and 169 are located adjacent opposite sides of the valving member 148 and project a short distance into the passage 130. The second pair of pivot members 171 and 172, shown in FIG. 12, comprise an upper or distal pivot member 171 and a lower or proximal pivot member 172. Members 171 and 172 are located adjacent opposite sides of the valving member 148 and project a short distance into the passage. The member 171 is opposite and in general alignment with the members 168. Member 172 is opposite and in general alignment with the pivot member 169.

Pivot member 168 has a fulcrum portion 173 facing the valving member 149 and an upwardly directed stop face 174. As shown in FIG. 12, pivot member 171 has a fulcrum portion 176 and an upwardly directed stop face 177. When the valving member 148 is in the open position, the outside surface of the valving member 148 engages the stop faces 174 and 177, thereby determining the full open position of the valving member 148. The lower pivot members 169 and 172 have outwardly directed stop faces 178 and 179 respectively. When the valving member 148 is in the open position, lower opposite portions of the valving member 148 engage the stop faces 178 and 179. Stop faces 174, 177, 178 and 179 determine the full open position of valving member 148.

The lower pivot members 169 and 172 have fulcrum portions 181 and 182 respectively that join the stop faces 178 and 179 to upwardly and inwardly inclined top surfaces or faces 183 and 184 respectively. Surfaces 183 and 184 function as stops or supports for holding the valving member 148 in its inclined, closed position as shown in FIG. 10.

The pivot and retaining means 167 has first and second pairs of upper and lower pivot members that are located adjacent opposite sides of the semi-circular base segments 128 and 129. These pivot members are identical to the pivot members 168, 169, 171 and 172. The pivot members of pivot and retaining means 167 that correspond to the pivot members 168, 169, 171 and 172 have the same reference numerals with the suffix A.

Referring to FIGS. 9 and 10, opposite side portions of the base 126 have upwardly directed side members 186 and 187. The side members 186 and 187 project away from the base in the direction of the flow of blood through the passage 130. Side member 186 is a generally triangular shape having inclined converging lips or shoulders 188 and 188A. The shoulders 188 and 188A are stop edges or seats which engage outer or side portions of the valving members 148 and 149 when the valving members 148 and 149 are in the closed positions. Side member 187 has a generally triangular shape and a pair of converging shoulders or lips 189 and 189A forming stops or seats for opposite sides of the valving members 148 and 149 respectively.

Side member 186 is located in the midportion of base segment 128 and midway between pivot members 168 and 168A. Side member 187 is located in the midportion of base segment 129 and midway between pivot members 171 and 171A.

The valving members 148 and 149 have an outer peripheral arcuate curvature that is smaller than the adjacent curvature of the inside wall 127 of the base. When the valving members 148 and 149 are in their closed positions, as shown in FIGS. 9 and 10, the transverse edges 154 and 154A are spaced from each other by a transverse linear space 191. The arcuate outer peripheral edges 153 and 153A of the valving members 149 and 149, respectively, are spaced with an arcuate space 192 from the adjacent inside wall 127 of the base 126. The spaces 191 and 192 permit a limited amount of reverse flow or backflow of blood through the passage 130 when the valving members 148 and 149 are in their closed position. The continuous movement of blood through the passage minimizes the stagnation of the blood and provides for continuous washing of the surfaces with the moving blood of the valving members 148 and 149, the pivot members 168, 169, 168A, 169A, 171, 172, 171A and 172A, and the inside wall 127 of the base 126.

Referring to FIGS. 11 and 12, valving members 148 and 149 are in their full or maximum open positions and divide the passage 130 into a central unobstructed area 193 and a first or right side area 194 between the valving member 148 and the inside wall 127 of the base segments 128 and 129. The valving member 149 forms a second or left passage 196 with the opposite portions of the inside wall of the segments 128 and 129. The blood flows past the opposite surfaces of both valving members 148 and 149, and flows around the continuous uninterrupted outer peripheral edges 153 and 153A thereby washing both side surfaces as well as the outer peripheral arcuate edges of the valving members 148 and 149 and the ears 156, 156A, 157 and 157A.

The valving members 148 and 149 are assembled on the base segments 128 and 129 by positioning the segments in a circle about the members 148 and 149. Parts of the valving members 148 and 149 are located in the spaces between the pairs of pivot members with the ears 156, 157, 156A and 157A located below the upper or distal pivot members 168, 171, 168A and 171A. Sleeve 134 is then placed around the circular-arranged base segments 128 and 129. The nipples 139 on the segments 128 and 129 are circumferentially aligned with the holes 138 in the sleeve 134. The segments 128 and 129 are then forced into the sleeve 134 until the top surface 143 of the sleeve abuts against the inside of flange 133. The ends 131 and 132 of segments 128 and 129 are in firm flat engagement with each other. The nipples 139 project into the holes 138 to hold the segments 128 and 129 with a force fit within the sleeve 134. The valving members 148 and 149 are generally balanced about their pivot axes on the pairs of pivot members 168, 169, 171 and 172 and 168A, 169A; 171A, 172A.

In use, the heart valve prosthesis 125 is connected to the heart tissue with a suitable suturing member. The heart valve prosthesis 125 functions on an increase in the blood pressure in the left atrium to open both valving members 148 and 149. Assuming the valving members 148 and 149 in their closed positions, as shown in FIGS. 9 and 10, an increase in the blood pressure on the proximal or lower side of the prosthesis will initially raise the valving members 148 and 149 to up positions away from pivot members 169, 172, 169A and 172A as shown by broken lines in FIG. 10. The pairs of ears 156, 157 and 156A, 157A engage the fulcrum surfaces 173, 176 and 173A, 176A of the upper or downstream pivot members 168, 171 and 168A, 171A respectively. The valving members 148 and 149 move around the fulcrum surfaces in separate opposite arcuate paths away from each other until the valving members 148 and 149 are in their open positions as shown in FIGS. 11 and 12. The valving members 128 and 129 pivot about separate cordial axes. These axes are parallel to each other during the opening and closing of the valve members. During the opening movements of the valve members, the pivot axes are determined by the fulcrum portions 173, 176 and 173A, 176A of the pivot members 168, 171 and 168A, 171A. During the closing movements of the valving members 128 and 129, the pivot axes shift to the lower sides of the members and are determined by the fulcrum surfaces 181, 182 and 181A, 182A of proximal pivot members 169, 172 and 169A, 172A. The closing pivot axes of the valving members 148 and 149 also shift toward each other as the members 148 and 149 close.

When the valving members 148 and 149 are in their open position, they are at a slight angle with respect to the longitudinal axis of the passage 130 whereby providing a minimum of interference to the flow of blood through the passage portions 193, 194 and 196. When valving members 148 and 149 are in their open position, opposite portions of the outside surfaces of the valving members engage the stop faces 174, 178, 177 and 179. In a similar manner, the valving member 149, which in the open position, engages the stop faces 174A, 178A, 177A and 179A of the two pairs of pivot members 168A, 169A and 171A, 172A respectively.

On a reduction of blood pressure in the left atrium or proximal side of the heart valve prosthesis 125, the blood pressure across the heart valve prosthesis is decreased and the flow of blood is reversed. The reverse flow of blood will quickly close the valving members 148 and 149 to their closed position as shown in FIGS. 9 and 10. The valving members, on the initial reverse flow of blood through passage 130, will drop a slight distance until opposite portions of the outer edges 153 and 153A engage the inside wall 127 and move around the arcuate fulcrum surfaces 181, 181A, 182 and 182A of the lower or proximate pivot members 169, 169A, 172, and 172A. When the valving member 148 is in its full closed position, the bottom side surface 152 is portioned and engageable with the inclined top surfaces 183 and 184 of the pivot members 169 and 172 and the shoulders or stops 188 and 189 of the side members 186 and 187. In a similar manner, the valving member 149 when in the full closed position engages the inclined surfaces 183A and 184A of the pivot members 169A and 172A and the inclined shoulders or stops 188A and 189A of the side members 186 and 187.

Figure 18:
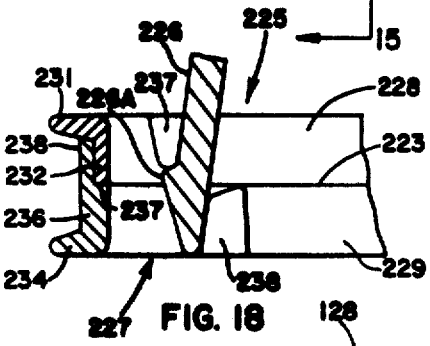
FIG. 18 is a fragmentary sectional view of a heart valve prosthesis having a two part base.

Referring to FIG. 18, there is shown a part of a heart valve prosthesis of the invention indicated generally at 225. Prosthesis 225 is similar to [prothesis] *prosthesis* 125 shown in FIGS. 9–12 and it has two valving members 226 (one shown) movably mounted on an annular base 227. Valving member 226 is shown in its full open position similar to FIG. 12. Base 227 has two annular parts or sleeves 228 and 229 that are secured together to form the base. Examples of heart valve prostheses having annular bases made of two parts are shown by Servelle in British Pat. No. 1,160,008 and Child in U.S. Pat. Nos. 3,835,475 and 3,825,956. Sleeves 228 and 229 have continuous inside surfaces providing the passage through the base. Sleeve 228 has an outwardly directed flange 231 attached to a cylindrical body 232 terminating in a circumferential edge 223. Sleeve 229 has an outwardly directed flange 234 attached to a cylindrical body 236. A suitable suturing member (not shown) located between the flanges is used to attach the base to heart tissue.

Body 236 has a circumferential shoulder 237 located in engagement with edge 223 and an annular lip 238 surrounding body 232. Bonding material, such as adhesives or the like, secure the lip 238 to body 232. Other types of connecting structures can be used to secure base sleeve 228 and 229 together. Base sleeves 228 and 229 can be solid metal or a core covered with a skin of pyrolytic carbon.

Upper or distal pivot projections or members 237 (one shown) and the side members, as side members 186 and 187 in FIG. 11, are part of the sleeve 228. Lower or proximal pivot projections or members 238 (one shown) are part of the sleeve 229. Each sleeve 228 and 229 has four pivot members. These pivot members have the same shape as pivot members 157, 157A, 168, 168A and 169, 169A, 172, 172A, shown in FIGS. 10 and 12.

The two part base enable the valving members 226 to be assembled in the base passage between the pairs of pivot members without adding parts or welding members to the base. The sleeves 228 and 229 are telescoped together locating the valving members 226 in operating positions between their respective pairs of pivot members. Each valving member has a pair of eyes 226A that engage the upper pivot members to retain the valving members 226 in assembled relation with the base 225.

While there has been shown and described three embodiments of the heart valve prosthesis of the invention, it is understood that changes in size, materials and structure can be made by those skilled in the art without departing from the invention.

The embodiments of the invention in which an exclusive property or privilege is claimed are defined as follows:

1. A heart valve prosthesis comprising: a base having an inside annular wall surrounding a passage for carrying blood through the base, means for connecting the base to heart tissue, valving means located in the passage for controlling the flow of blood through the passage, said valving means comprising a first valving member having a convex curved leading edge and a transverse trailing edge, and a second valving member having a convex curved leading edge and a transverse trailing edge, first pivot means pivotally connecting the first member to the base for movement about a first axis offset in one direction from the center of the passage, second pivot means pivotally connecting the second member to the base for movement about a second axis offset in the direction opposite the one direction from the center of the passage, a first side member on the base projected in the direction of the flow of blood through the passage, a second side member on the base projected in the direction of the flow of blood through the passage, said second side member being opposite the first side member, each side member having first stop means engageable with the first valving member and second valving member to hold the first valving member and second valving member in inclined closed positions to restrict the flow of blood in one direction through the passage, and second stop means on the base engageable with the first valving member and the second valving member when the valving members are in their open positions.

2. The prosthesis of claim 1 wherein: the first valving member and second valving member are inclined toward each other when in their closed positions.

3. The prosthesis of claim 2 wherein: the inclination is about 45° from the transverse plane of the passage.

4. The prosthesis of claim 1 wherein: each side member has an inside surface coextensive with the inside annular wall of the base.

5. The prosthesis of claim 1 wherein: the first stop means comprise inclined and converging lip portions providing seats engageable with parts of the valving members when the valving members are in their closed positions:

6. The prosthesis of claim 1 wherein: the second stop means comprise projections extended from the base engageable with parts of the valving members when the valving members are in their open positions.

7. The prosthesis of claim 1 wherein: each side member has a generally triangular shape.

8. The prosthesis of claim 1 wherein: each valving member has a leading edge having a thickness about twice the thickness of the trailing edge, and generally flat side surfaces between the leading and trailing edges.

9. The prosthesis of claim 1 wherein: each valving member is substantially balanced on its respective pivot means.

10. The prosthesis of claim 1 wherein: the side members are located between the first axis and the second axis.

11. The prosthesis of claim 1 wherein: the transverse trailing edges of the valving members are spaced apart when the valving members are in their closed positions.

12. The prosthesis of claim 1 wherein: each valving member has outer peripheral edges spaced from the inside wall to allow limited reverse flow of blood between the valving members and the base when the valving members are in the closed positions.

13. The prosthesis of claim 1 wherein: the means for connecting the base to heart tissue includes a sleeve, and coacting means on the base and sleeve allowing the base to be removed from the sleeve after the means is connected to the heart tissue.

14. The prosthesis of claim 1 wherein: the first pivot means and the second means each includes pivot axles secured to opposite side edges of the first and second valving members, said pivot axles being located along a transverse pivot axis parallel to the linear trailing edges of the valving members, said transverse pivot axis being spaced from the midportions of the leading edges and trailing edges of the members.

15. The prosthesis of claim 14 wherein: the distance from the pivot axes to the midpoint of the trailing edge is about twice the distance from the pivot axis to the midpoint of the leading edge .

16. The prosthesis of claim 1 wherein: the means for connecting the base to heart tissue includes a sleeve having a cylindrical inside wall, an inside threaded section and an inside shoulder between the inside wall and the inside threaded section, said base having an outside wall and an outside threaded section and a shoulder between said outside wall and and outside threaded section, said inside and outside walls, threaded sections and shoulders engaging each other when the base is mounted on the sleeve, said sleeve having an outside annular channel, a suturing collar located in the channel adapted to be secured to heart tissue, and releasable lock means mounted on the sleeve and engageable with the base to fix the position of the base on the sleeve, said lock means having a lock position to fix the location of the base on the sleeve and a release position allowing the base to be mounted on and removed from the suturing means after the suturing means is attached to the heart tissue.

17. The prosthesis of claim 1 wherein: the means for connecting the base to heart tissue includes a sleeve, coacting means on the base and sleeve allowing the base to be removed from the sleeve after the means is connected to the heart tissue, and lock means for locking the sleeve on the base, said lock means being movable to a release position to allow the base to be removed from the sleeve without removing the sleeve from the heart tissue.

18. The prosthesis of claim 1 wherein: the first pivot means includes a first pair of pivot members secured to the base and projected into the passage and a second pair of pivot members secured to the base and projected into the passage, each pair of pivot members having one pivot member located adjacent one side of the first valving member and a second pivot member located adjacent the opposite side of the first valving member, and means on the first valving member cooperating with a pivot member of each pair of pivot members to control the the pivotal movement of the first valving member and retain the first valving member in assembled relation with the base, the second pivot means includes a first pair of pivot members secured to the base and projected into the passage and a second pair of pivot members secured to the base and projected into the passage, each pair of the pivot members of the second pivot means having one pivot member located adjacent one side of the second valving member and another pivot member located adjacent the opposite side of the second valving member, and means on the second valving member cooperating with a pivot member of each pair of pivot members of the second pivot means to control the pivotal movement of the second valving member and retain the second valving member in assembled relation with the base.

19. The prosthesis of claim 18 wherein: the means on the first valving member comprise a pair of ears on opposite side portions of the first valving member, and the means on the second valving member comprise a pair of ears on opposite side portions of the second valving member.

20. The prosthesis of the claim 1 wherein: the base has first and second semi-circular segments, and annular means holding the segments in a circular arrangement.

21. The prosthesis of claim 20 wherein: the first pivot means includes a first pivot member on the first segment and a second pivot member on the second segment, and the second pivot means includes a first pivot member on the first segment and a second pivot member on the second segment.

22. A heart valve prosthesis comprising: a base having an inside annular wall surrounding a passage for carrying blood through the base, valving means located in the passage movable to open and closed positions for controlling the flow of blood through the passage, said valving means comprising a first valving member having a convex curved leading edge and a transverse trailing edge, and a second valving member having a convex curved leading edge and a transverse trailing edge, first pivot means pivotally associating the first member with the base, said first pivot means having fulcrum portions engageable with the first valving member for controlling the movement of the first valving member in a location offset in one direction from the center of the passage, second pivot means pivotally associating the second member with the base, said second pivot means having fulcrum portions engageable with the second valving member for controlling the movement of the second valving member in a location offset in the direction opposite the one direction from the center of the passage, a first side member on the base projected in the direction of the flow of blood through the passage, a second side member on the base projected in the direction of the flow of blood through the passage, said second side member being opposite the first side member, each side member having first stop means engageable with the first valving member and second valving member to hold the first valving member and second valving member in inclined closed positions to restrict the flow of blood in one direction through the passage, and said first and second pivot means having second stop means on the base engageable with the first valving member and the second valving member when the valving members are in their open positions.

23. The prosthesis of claim 22 wherein: the first valving member and second valving member are inclined toward each other when in their closed positions.

24. The prosthesis of claim 22 wherein: each side member has an inside surface coextensive with the inside annular wall of the base.

25. The prosthesis of claim 22 wherein: the first stop means comprise inclined and converging lip portions providing seats engageable with parts of the valving members when the valving members are in their closed positions.

26. The prosthesis of claim 22 wherein: each valving member has a leading edge having a thickness about twice the thickness of the trailing edge, and generally flat side surfaces between the leading and trailing edges.

27. The prosthesis of claim 22 wherein: the transverse trailing edges of the valving members are spaced apart when the valving members are in their closed positions.

28. The prosthesis of claim 22 wherein: each valving member has outer peripheral edges spaced from the inside wall to allow limited reverse flow of blood between the valving members and the base when the valving members are in the closed positions.

29. The prosthesis of claim 22 wherein: the first pivot means and the second pivot means each includes first and second pairs of pivot members on the base and ears on the valving members associated with the pairs of pivot members cooperating with a pivot member of each pair of pivot members to control the movement of the valving members.

30. The prosthesis of claim 22 wherein: the base has first and second semi-circular segments, and annular means holding the segments in a circular arrangement, said first pivot and second pivot means each having a first pivot member on the first segment and a second pivot member on the second segment.

31. A heart valve prosthesis comprising: a base having first and second semi-circular segments defining an inside annular wall surrounding a passage for carrying blood through the base and annular means holding said segments in circular arrangement, valving means movable to open and closed positions for controlling the flow of blood through the passage, said valving means comprising a first valving member and a second valving member, means cooperating with the valving members for controlling the opening and closing movements of the valving members and retaining the valving members in operative assembled relation with the base, said means cooperating with the valving members including first pivot means movably associating the first valving member with the base, said first pivot means having first and second pairs of pivot members secured to the base and engageable with separate portions of the first valving member, said first valving member having means cooperating with the first and second pairs of pivot members to retain the first valving member in assembled relation with the base, second pivot means movably associating the second valving member with the base, said second pivot means having first and second pairs of pivot members secured to the base and engageable with separate portions of the second valving member, said second valving member having means cooperating with the first and second pair of pivot members of the second pivot means to retain the second valving member in assembled relation with the base, said first pairs of pivot members of the pivot means being joined to said first segment and said second pairs of pivot members of said pivot means being joined to said second segment and side members on the base projected in the direction of flow of blood through the passage, said side members having stop portions engageable with the first and second valving members when said first and second valving members are in their closed positions.

32. The prosthesis of claim 31 wherein: the first valving member and second valving member are inclined toward each other when in their closed positions.

33. The prosthesis of claim 31 wherein: the stop portions comprise inclined and converging lip portions providing seats engageable with parts of the valving members when the valving members are in their closed positions.

34. The prosthesis of claim 31 wherein: each side member has a generally triangular shape.

35. The prosthesis of claim 31 wherein: each valving member has a leading edge having a thickness about twice the thickness of the trailing edge, and generally flat side surfaces between the leading and trailing edges.

36. The prosthesis of claim 31 wherein: each valving member is substantially balanced on its respective pivot means.

37. The prosthesis of claim 31 wherein: each valving member has outer peripheral edges spaced from the inside wall to allow limited reverse flow of blood between the valving members and the base when the valving members are in the closed positions.

38. The prosthesis of claim 31 wherein: the first valving member pivots about a first location offset from the center of the passage and the second valving member pivots about a second location offset from the center of the axis, said first and second locations being located on opposite sides of the center of the passage and extended generally parallel to each other.

39. The prosthesis of claim 38 wherein: the side members are located between the first location and the second location.

40. A valving member for a heart valve prosthesis comprising: a semi-elliptical shaped member having a convex curved leading edge, a transverse linear trailing edge, arcuate side edges connecting the opposite sides of the leading edge to opposite ends of the trailing edge and generally flat side surfaces extended from the leading edge to the trailing edge.

41. The valving member of claim 40 including: pivot axles secured to opposite side edges of the member, said pivot axles located along a transverse pivot axis parallel to the linear trailing edge, said pivot axis being spaced from the midportions of the leading edge and trailing edge.

42. The valving member of claim 41 wherein: the distance from the pivot axis to the midportion of the trailing edge is about twice the distance from the pivot axis to the midportion of the leading edge.

43. The valving member of claim 40 wherein: said side surfaces taper toward each other from the leading edge to the trailing edge of the member.

44. The valving member of claim 40 including: a pair of ears projected outwardly from separate portions of the side surfaces of the member, said ears being located adjacent opposite portions of the side edges of the member.

45. The valving member of the claim 44 wherein: each ear has a trailing face extended generally parallel to the transverse linear edge of the member.

46. The valving member of claim 45 wherein: the trailing faces of the ears are located along a line, said line being located generally a distance from the trailing edge that is twice the distance between the line and the midportion of the leading edge.

47. The valving member of claim 44 wherein: each ear has an outwardly inclined ramp extended toward the trailing edge of the member.

48. A heart valve prosthesis comprising: a base having an inside annular wall surrounding a passage for carrying blood through the base, means for connecting the base to heart tissue, said means including first means and second means for connecting the first means to heart tissue, and coacting means on the base and first means operable to permit removal of the base from the first means after the first means is connected to heart tissue, valving means for controlling the flow of blood through the passage, said valving means comprising a first valving member and a second valving member, first pivot means pivotally mounting the first valving member on the base, second pivot means pivotally mounting the second valving member on the base, and side members on the base projected in the direction of flow of blood through the passage, said side members having stop means engageable with the first and second valving members when said first and second valving members are in their closed positions.

49. The prosthesis of claim 48 wherein: the first valving member and second valving member are inclined toward each other when in their closed positions.

50. The prosthesis of claim 49 wherein: the inclination is about 45° from the transverse plane of the passage.

51. The prosthesis of claim 48 wherein: the stop means includes a pair of side projections located on opposite sides of the base, each projection having portions that are engaged by the members when the members are in their closed positions.

52. The prosthesis of claim 48 wherein: the stop means comprise inclined and converging lip portions providing seats engageable with parts of the valving members when the valving members are in their closed positions.

53. The prosthesis of claim 48 including: second stop means comprising projections extended from the base engageable with parts of the valving members when the valving members are in their open positions.

54. The prosthesis of claim 48 wherein: each side member has a generally triangular shape.

55. The prosthesis of claim 48 wherein: each valving member has a leading edge having a thickness about twice the thickness of the trailing edge, and generally flat side surfaces between the leading and trailing edges.

56. The prosthesis of claim 47 wherein: each valving member is substantially balanced on its respective pivot means.

57. The prosthesis of claim 48 wherein: each valving member has outer peripheral edges spaced from the inside wall to allow limited reverse flow of blood between the valving members and the base when the valving members are in the closed positions.

58. The prosthesis of claim 48 wherein: the means for connecting the base to heart tissue includes a sleeve, and coacting means on the base and sleeve allowing the base to be removed from the sleeve after the means is connected to the heart tissue.

59. The prosthesis of claim 48 wherein: the first valving member pivots about a first axis offset from the center of the passage and the second valving member pivots about a second axis offset from the center of the [axis] *passage*, said first and second axes being located on opposite sides of the center of the passage and extended generally parallel to each other.

60. The prosthesis of claim 59 wherein: the side members are located between the first axis and the second axis.

61. A heart valve prosthesis comprising: a base having a pair of semi-circular segments located in a circular arrangement, said segments having an inside annular wall forming a passage through the base, annular means surrounding the segments for holding the segments in the circular arrangement, valving means movable to open and closed positions for controlling the flow of blood through said passage, and means secured to the segments cooperating with the valving means to hold the valving means in assembled relation with the base and controlling the opening and closing movements of the valving means.

62. The prosthesis of claim 61 wherein: the annular means is a circular sleeve having a plurality of holes, and said segments are provided with projections which extend into the holes.

63. The prosthesis of claim 62 wherein: the valving means includes two valving members and the means secured to the segments are pairs of pivot members cooperating with the valving members to hold the valving member on the base.

64. The prosthesis of claim 62 wherein: each segment has two pairs of pivot members, one pair cooperating with one valving member and the other pair cooperating with the second valving member whereby each valving member is controlled by two pairs of pivot members.

*65. A heart valve prosthesis comprising: a base having an inside annular wall surrounding a passage for carrying blood through the base, means for connecting the base to heart tissue, valving means located in the passage operable to allow substantially unrestricted flow of blood in a first direction through the passage and to restrict the flow of blood in a second direction through the passage, said second direction being opposite the first direction, said valving means comprising a first valving member having a convex curved edge and a transverse edge, and a second valving member having a convex curved edge and a transverse edge, said first and second valving members when in their closed positions being obliquely inclined in opposite directions with respect to the longitudinal axis of the passage through the base, and said transverse edges being located adjacent each other, each valving member having an outer periphery having portions thereof spaced from the inside annular wall to allow limited flow of blood in the second direction between the valving members and the inside annular wall when the valving members are in their closed positions, first ear means on the first valving member, first pivot means pivotally connecting the first valving member to the base for movement about a first axis offset in one direction from the center of the passage, said first pivot means including said first ear means and first fulcrum portions on the base, said first ear means being engageable with the first fulcrum portions for controlling the movement of the first valving member between its open and closed positions, second ear means on the second valving member, and second pivot means pivotally connecting the second valving member to the base for movement about a second axis offset in a direction opposite the one direction from the center of the passage, said second pivot means including said second ear means and second fulcrum portions on the base, said second ear means being engageable with the second fulcrum portions for controlling the movement of the second valving member between its open and closed positions, said first and second axes being generally parallel to each other, said base including a first side member and a second side member, said first and second side members forming barriers adjacent opposite sides of the first and second valving members when the valving members are in their closed positions to minimize the flow of blood through the passage in the second direction, first stop means engageable with the first valving member and second valving member to hold the first valving member and second valving member in their closed positions to restrict the flow of blood in the second direction through the passage, and second stop means engageable with the first valving member and second valving member when the valving members are in their open positions to allow substantially free flow of blood through the passage in the first direction.*

*66. The prosthesis of claim 65 wherein: each side member has an inside surface coextensive with the inside annular wall.*

*67. The prosthesis of claim 65 wherein: each valving member has opposite side portions, said first ear means being secured to the opposite side portions of the first valving member, and said second ear means being secured to the opposite side portion of the second valving member.*

*68. The prosthesis of claim 65 wherein: each side member includes converging side edges.*

*69. The prosthesis of claim 68 wherein: each side member has a convex curved outer surface.*

*70. A heart valve prosthesis comprising: base means having an inside annular wall surrounding a passage for carrying blood through the base means, a first side member, and a second side member opposite the first side member, valve means located in the passage operable to allow substantially unrestricted flow of blood in a first direction through the passage and to restrict the flow of blood in a second direction through the passage, said second direction being opposite the first direction, said valve means comprising a first valving member having a convex curved edge, opposite side edges, a transverse edge, and first ear means adjacent the opposite side edges, and a second valving member having a convex curved edge, opposite side edges, a transverse edge, and a second ear means adjacent the opposite side edges of the second valving member, first pivot means pivotally associating the first valving member with the base means, said first pivot means including the first ear means and fulcrum portions of the base means, said first ear means being engageable with the fulcrum portions*

*for controlling the movement of the first valve member in a location offset in one direction from the center of the passage, second pivot means pivotally associating the second valving member with the base means, said second pivot means including the second ear means and fulcrum portions on the base means, said second ear means being engageable with the fulcrum portion of the second pivot means for controlling the movement of the second valving means in a location offset in a second direction opposite the first direction from the center of the base, said first and second valving members concurrently pivoting between open and closed positions to control the flow of blood through the passage of the base means, said first and second valving members when in their closed positions being inclined in opposite directions with respect to the longitudinal axis of the passage, and said transverse edges of the first and second valving members being located adjacent each other, said base means having first stop means engageable with the first valving member and the second valving member to limit pivotal movement of the first valving member and second valving member to their opposite inclined closed positions to restrict the flow of blood in the second direction through the passage, and second stop means on the base means engageable with the first valving member and second valving member to limit pivotal movement of the first and second valving members to open positions.*

*71. The prosthesis of claim 70 wherein: each side member has an inside surface coextensive with the inside annular wall.*

*72. The prosthesis of claim 70 wherein: the transverse edges of the first and second valving members are spaced apart when the valving members are in their closed positions.*

*73. The prosthesis of claim 70 wherein: each valving member has an outer peripheral edge spaced from the inside wall to allow limited flow of blood in the second direction between the valving members and the inside annular wall when the first and second valving members are in their closed positions.*

*74. The prosthesis of claim 70 wherein: said first stop means includes a first stop face engageable with the first valving member and a second stop face engageable with the second valving member when the first and second valving members are in their closed positions.*

*75. The prosthesis of claim 70 wherein: said second stop means includes a first stop face engageable with the first valving member and a second stop face engageable with the second valving member when the first and second valving members are in their open positions.*

*76. The prosthesis of claim 70 including: means on the base means for connecting the base means to heart tissue.*

*77. A heart valve prosthesis comprising: a base having an inside annular wall surrounding a passage for carrying blood through the base, said passage having a longitudinal central axis, said base including a first side member projected generally parallel to the longitudinal axis of the passage, and a second side member opposite the first side member projected generally parallel to the longitudinal axis of the passage, means mounted on the base for connecting the base to heart tissue, valving means located in the passage operable to allow substantially unrestricted flow of blood in a first direction through the passage and to restrict the flow of blood in a second direction through the passage, said second direction being opposite the first direction, said valving means comprising a first valving member having a convex curved edge, a transverse edge, and first ears, a second valving member having a convex curved edge, a transverse edge, and second ears, first pivot means pivotally associating the first valving member with the base for movement about a first axis offset in one direction from the center of the passage, said first pivot means including said first ears and first fulcrum portions on the base, said first ears being engageable with the first fulcrum portions for controlling the movement of the first valving member between its open and closed positions, second pivot means pivotally associating the second valving member with the base for movement about a second axis offset in a direction opposite the one direction from the center of the passage, said second pivot means including said second ears and second fulcrum portions on the base, said second ears being engageable with the second fulcrum portions for controlling the movement of the second valving member between its open and closed positions, said first and second valving members concurrently pivoting between open and closed positions to control the flow of blood through the passage of the base, said first and second valving members when in their closed positions being obliquely inclined in opposite directions with respect to the longitudinal axis of the passage, and said transverse edges of the first and second valving members being located adjacent each other, said base having first stop means engageable with the first valving member and the second valving member to limit pivotal movement of the first valving member and the second valving member to opposite obliquely inclined closed positions to restrict the flow of blood in the second direction through the passage, said base further including second stop means engageable with the first valving member and second valving member to limit pivotal movement of the first and second valving members to open positions.*

*78. The prosthesis of claim 77 wherein: each side member has an inside surface coextensive with the inside annular wall.*

*79. The prosthesis of claim 77 wherein: each valving member has an outer peripheral edge spaced from the inside annular wall to allow limited flow of blood in the second direction between the valving members and the inside annular wall of the base when the valving members are in their closed positions.*

*80. The prosthesis of claim 77 wherein: each valving member has opposite side portions, said first ears being secured to opposite side portions of the first valving member, said second ears being secured to opposite side portions of the second valving member.*

*81. The prosthesis of claim 77 wherein: said first stop means includes a first stop face engageable with the first valving member and second stop face engageable with the second valving member when the first and second valving members are in their closed positions.*

*82. The prosthesis of claim 77 wherein: the second stop means includes a first stop face engageable with the first valving member and a second stop face engageable with the second valving member when the valving members are in their open positions.*

* * * * *